(12) United States Patent
Lashinski

(10) Patent No.: US 8,974,489 B2
(45) Date of Patent: *Mar. 10, 2015

(54) DUAL ENDOVASCULAR FILTER AND METHODS OF USE

(75) Inventor: Randall T. Lashinski, Santa Rosa, CA (US)

(73) Assignee: Claret Medical, Inc., Santa Rosa, CA (US)

( * ) Notice: Subject to any disclaimer, the term of this patent is extended or adjusted under 35 U.S.C. 154(b) by 14 days.

This patent is subject to a terminal disclaimer.

(21) Appl. No.: 13/383,488

(22) PCT Filed: Jul. 27, 2010

(86) PCT No.: PCT/US2010/043390
§ 371 (c)(1),
(2), (4) Date: Mar. 23, 2012

(87) PCT Pub. No.: WO2011/017103
PCT Pub. Date: Feb. 10, 2011

(65) Prior Publication Data
US 2012/0179195 A1 Jul. 12, 2012

Related U.S. Application Data

(60) Provisional application No. 61/228,703, filed on Jul. 27, 2009.

(51) Int. Cl.
*A61M 29/00* (2006.01)
*A61F 2/01* (2006.01)

(52) U.S. Cl.
CPC ........... *A61F 2/013* (2013.01); *A61F 2002/011* (2013.01); *A61F 2002/018* (2013.01); *A61F 2230/001* (2013.01); *A61F 2230/0078* (2013.01); *A61F 2230/0095* (2013.01)
USPC .......................................................... 606/200

(58) Field of Classification Search
CPC .................................. A61F 2/01; A61F 2/013
USPC ................................................. 606/200, 127
See application file for complete search history.

(56) References Cited

U.S. PATENT DOCUMENTS

| | | | |
|---|---|---|---|
| 3,472,230 A | 10/1969 | Fogarty | |
| 4,619,246 A | 10/1986 | Molgaard-Nielsen et al. | |
| 4,630,609 A | 12/1986 | Chin | |
| 4,650,466 A | 3/1987 | Luther | |
| 4,706,671 A | 11/1987 | Weinrib | |
| 4,723,549 A | 2/1988 | Wholey | |
| 4,873,978 A | 10/1989 | Ginsburg | |

(Continued)

FOREIGN PATENT DOCUMENTS

| | | |
|---|---|---|
| DE | 10049812 | 4/2002 |
| EP | 1400257 | 3/2004 |

(Continued)

OTHER PUBLICATIONS

International Search Report in Application No. PCT/US2010/021417 dated Aug. 23, 2010, in 4 pages.

(Continued)

*Primary Examiner* — Gregory Anderson
(74) *Attorney, Agent, or Firm* — Knobbe Martens Olson & Bear LLP

(57) ABSTRACT

Blood filter devices and methods of use.

15 Claims, 8 Drawing Sheets

(56) References Cited

U.S. PATENT DOCUMENTS

| | | | |
|---|---|---|---|
| 5,108,419 A | 4/1992 | Reger | |
| 5,192,286 A | 3/1993 | Phan | |
| 5,348,545 A | 9/1994 | Shani et al. | |
| 5,381,782 A | 1/1995 | DeLaRama et al. | |
| 5,395,327 A | 3/1995 | Lundquist et al. | |
| 5,613,980 A | 3/1997 | Chauhan | |
| 5,624,430 A | 4/1997 | Eton et al. | |
| 5,662,671 A | 9/1997 | Barbut et al. | |
| 5,707,389 A | 1/1998 | Louw et al. | |
| 5,766,151 A | 6/1998 | Valley et al. | |
| 5,779,716 A | 7/1998 | Cano et al. | |
| 5,814,064 A | 9/1998 | Daniel | |
| 5,827,324 A | 10/1998 | Cassell | |
| 5,833,650 A | 11/1998 | Imran | |
| 5,848,964 A | 12/1998 | Samuels | |
| 5,897,819 A | 4/1999 | Miyata et al. | |
| 5,910,154 A * | 6/1999 | Tsugita et al. | 606/200 |
| 5,910,364 A | 6/1999 | Miyata et al. | |
| 5,911,734 A | 6/1999 | Tsugita et al. | |
| 5,935,139 A | 8/1999 | Bates | |
| 5,980,555 A | 11/1999 | Barbut et al. | |
| 5,993,469 A | 11/1999 | McKenzie et al. | |
| 6,001,118 A | 12/1999 | Daniel | |
| 6,010,522 A | 1/2000 | Barbut et al. | |
| 6,027,520 A | 2/2000 | Tsugita et al. | |
| 6,042,598 A | 3/2000 | Tsugita et al. | |
| 6,080,140 A | 6/2000 | Swaminathan et al. | |
| 6,083,239 A | 7/2000 | Addis | |
| 6,096,053 A | 8/2000 | Bates | |
| 6,099,534 A | 8/2000 | Bates | |
| 6,120,494 A | 9/2000 | Jonkman | |
| 6,142,987 A | 11/2000 | Tsugita | |
| 6,152,946 A | 11/2000 | Broome et al. | |
| 6,171,328 B1 | 1/2001 | Addis | |
| 6,179,851 B1 | 1/2001 | Barbut et al. | |
| 6,235,045 B1 | 5/2001 | Barbut et al. | |
| 6,245,087 B1 | 6/2001 | Addis | |
| 6,245,088 B1 | 6/2001 | Lowery | |
| 6,245,089 B1 | 6/2001 | Daniel | |
| 6,264,663 B1 | 7/2001 | Cano | |
| 6,270,513 B1 | 8/2001 | Tsugita et al. | |
| 6,277,138 B1 | 8/2001 | Levinson et al. | |
| 6,309,399 B1 * | 10/2001 | Barbut et al. | 606/159 |
| 6,325,815 B1 | 12/2001 | Kusleika | |
| 6,336,934 B1 | 1/2002 | Gilson et al. | |
| 6,346,116 B1 | 2/2002 | Brooks et al. | |
| 6,361,545 B1 | 3/2002 | Macoviak et al. | |
| 6,364,900 B1 | 4/2002 | Heuser | |
| 6,371,971 B1 | 4/2002 | Tsugita et al. | |
| 6,383,174 B1 | 5/2002 | Eder | |
| 6,383,205 B1 | 5/2002 | Samson et al. | |
| 6,440,120 B1 | 8/2002 | Maahs | |
| 6,485,502 B2 | 11/2002 | Don Michael | |
| 6,517,559 B1 * | 2/2003 | O'Connell | 606/200 |
| 6,558,356 B2 | 5/2003 | Barbut | |
| 6,595,983 B2 | 7/2003 | Voda | |
| 6,605,102 B1 | 8/2003 | Mazzocchi | |
| 6,620,148 B1 | 9/2003 | Tsugita | |
| 6,648,837 B2 | 11/2003 | Kato et al. | |
| 6,663,652 B2 | 12/2003 | Daniel et al. | |
| 6,676,682 B1 | 1/2004 | Tsugita et al. | |
| 6,712,834 B2 | 3/2004 | Yassour et al. | |
| 6,712,835 B2 | 3/2004 | Mazzocchi | |
| 6,726,651 B1 | 4/2004 | Robinson et al. | |
| 6,726,701 B2 | 4/2004 | Gilson | |
| 6,740,061 B1 | 5/2004 | Oslund | |
| 6,817,999 B2 | 11/2004 | Berube et al. | |
| 6,830,579 B2 | 12/2004 | Barbut | |
| 6,843,798 B2 | 1/2005 | Kusleika et al. | |
| 6,872,216 B2 | 3/2005 | Daniel | |
| 6,881,194 B2 | 4/2005 | Miyata et al. | |
| 6,887,258 B2 * | 5/2005 | Denison et al. | 606/200 |
| 6,905,490 B2 | 6/2005 | Parodi | |
| 6,907,298 B2 | 6/2005 | Smits et al. | |
| 6,969,396 B2 | 11/2005 | Krolik et al. | |
| 7,011,094 B2 | 3/2006 | Rapacki et al. | |
| 7,048,752 B2 | 5/2006 | Mazzocchi | |
| 7,094,249 B1 | 8/2006 | Broome | |
| 7,115,134 B2 | 10/2006 | Chambers | |
| 7,160,255 B2 | 1/2007 | Saadat | |
| 7,169,161 B2 | 1/2007 | Bonnette et al. | |
| 7,169,165 B2 | 1/2007 | Belef et al. | |
| 7,182,757 B2 | 2/2007 | Miyata et al. | |
| 7,214,237 B2 | 5/2007 | Don Michael | |
| 7,278,974 B2 | 10/2007 | Kato et al. | |
| 7,313,445 B2 | 12/2007 | McVenes et al. | |
| 7,323,001 B2 | 1/2008 | Clubb et al. | |
| 7,399,308 B2 | 7/2008 | Borillo et al. | |
| 7,410,491 B2 | 8/2008 | Hopkins | |
| 7,493,154 B2 | 2/2009 | Bonner et al. | |
| 7,559,925 B2 | 7/2009 | Goldfarb et al. | |
| 7,572,272 B2 * | 8/2009 | Denison et al. | 606/200 |
| 7,621,904 B2 | 11/2009 | McFerran et al. | |
| 7,766,961 B2 | 8/2010 | Patel et al. | |
| 7,918,859 B2 | 4/2011 | Katoh et al. | |
| 7,922,732 B2 | 4/2011 | Mazzocchi et al. | |
| 7,998,104 B2 | 8/2011 | Chang | |
| 8,372,108 B2 | 2/2013 | Lashinski | |
| 8,382,788 B2 | 2/2013 | Galdonik | |
| 8,518,073 B2 | 8/2013 | Lashinski | |
| 8,753,370 B2 | 6/2014 | Lashinski | |
| 2001/0041858 A1 | 11/2001 | Ray et al. | |
| 2002/0026145 A1 | 2/2002 | Bagaoisan et al. | |
| 2002/0055767 A1 | 5/2002 | Forde et al. | |
| 2002/0077596 A1 | 6/2002 | McKenzie et al. | |
| 2002/0095172 A1 | 7/2002 | Mazzocchi et al. | |
| 2002/0123761 A1 | 9/2002 | Barbut et al. | |
| 2002/0161394 A1 | 10/2002 | Macoviak et al. | |
| 2002/0165571 A1 | 11/2002 | Herbert et al. | |
| 2003/0100919 A1 | 5/2003 | Hopkins et al. | |
| 2003/0130684 A1 | 7/2003 | Brady et al. | |
| 2003/0171770 A1 | 9/2003 | Kusleika et al. | |
| 2004/0002730 A1 | 1/2004 | Denison et al. | |
| 2004/0044350 A1 | 3/2004 | Martin et al. | |
| 2004/0044360 A1 | 3/2004 | Lowe | |
| 2004/0064092 A1 | 4/2004 | Tsugita et al. | |
| 2004/0093015 A1 | 5/2004 | Ogle | |
| 2004/0167565 A1 | 8/2004 | Beulke et al. | |
| 2004/0193206 A1 | 9/2004 | Gerberding | |
| 2004/0215167 A1 | 10/2004 | Belson | |
| 2004/0220611 A1 | 11/2004 | Ogle | |
| 2004/0225321 A1 | 11/2004 | Krolik et al. | |
| 2004/0230220 A1 | 11/2004 | Osborne | |
| 2004/0243175 A1 | 12/2004 | Don Michael | |
| 2004/0254601 A1 | 12/2004 | Eskuri | |
| 2004/0254602 A1 | 12/2004 | Lehe et al. | |
| 2005/0010285 A1 | 1/2005 | Lambrecht et al. | |
| 2005/0065397 A1 | 3/2005 | Saadat et al. | |
| 2005/0080356 A1 | 4/2005 | Dapolito et al. | |
| 2005/0101987 A1 | 5/2005 | Salahieh | |
| 2005/0131449 A1 | 6/2005 | Salahieh et al. | |
| 2005/0137696 A1 | 6/2005 | Salahieh | |
| 2005/0177132 A1 | 8/2005 | Lentz et al. | |
| 2006/0015136 A1 | 1/2006 | Besselink | |
| 2006/0015138 A1 | 1/2006 | Gertner | |
| 2006/0030877 A1 | 2/2006 | Martinez et al. | |
| 2006/0041188 A1 | 2/2006 | Dirusso et al. | |
| 2006/0089666 A1 * | 4/2006 | Linder et al. | 606/200 |
| 2006/0100658 A1 | 5/2006 | Obana | |
| 2006/0100662 A1 | 5/2006 | Daniel et al. | |
| 2006/0129180 A1 | 6/2006 | Tsugita et al. | |
| 2006/0149350 A1 | 7/2006 | Patel et al. | |
| 2006/0161241 A1 | 7/2006 | Barbut et al. | |
| 2006/0200191 A1 | 9/2006 | Zadno-Azizi | |
| 2006/0259066 A1 | 11/2006 | Euteneuer | |
| 2007/0088244 A1 | 4/2007 | Miller et al. | |
| 2007/0088383 A1 | 4/2007 | Pal et al. | |
| 2007/0173878 A1 | 7/2007 | Heuser | |
| 2007/0191880 A1 * | 8/2007 | Cartier et al. | 606/200 |
| 2007/0244504 A1 | 10/2007 | Keegan et al. | |
| 2008/0004687 A1 | 1/2008 | Barbut | |
| 2008/0058860 A1 | 3/2008 | Demond et al. | |
| 2008/0065145 A1 | 3/2008 | Carpenter | |
| 2008/0065147 A1 | 3/2008 | Mazzocchi et al. | |

(56) References Cited

U.S. PATENT DOCUMENTS

| | | |
|---|---|---|
| 2008/0125848 A1 | 5/2008 | Kusleika et al. |
| 2008/0154153 A1 | 6/2008 | Heuser |
| 2008/0188884 A1 | 8/2008 | Gilson et al. |
| 2008/0234722 A1 | 9/2008 | Bonnette et al. |
| 2008/0262442 A1 | 10/2008 | Carlin et al. |
| 2008/0300462 A1 | 12/2008 | Intoccia et al. |
| 2009/0024072 A1 | 1/2009 | Criado et al. |
| 2009/0024153 A1 | 1/2009 | Don Michael |
| 2009/0069840 A1 | 3/2009 | Hallisey |
| 2009/0198269 A1 | 8/2009 | Hannes et al. |
| 2009/0203962 A1 | 8/2009 | Miller et al. |
| 2009/0254172 A1 | 10/2009 | Grewe et al. |
| 2009/0287187 A1 | 11/2009 | Legaspi et al. |
| 2009/0326575 A1 | 12/2009 | Galdonik |
| 2010/0004633 A1 | 1/2010 | Rothe et al. |
| 2010/0063537 A1 | 3/2010 | Ren et al. |
| 2010/0179583 A1 | 7/2010 | Carpenter et al. |
| 2010/0179584 A1 | 7/2010 | Carpenter et al. |
| 2010/0179585 A1 | 7/2010 | Carpenter et al. |
| 2010/0179647 A1 | 7/2010 | Carpenter et al. |
| 2010/0185216 A1 | 7/2010 | Garrison et al. |
| 2010/0185231 A1 | 7/2010 | Lashinski |
| 2010/0191276 A1 | 7/2010 | Lashinski |
| 2010/0211095 A1 | 8/2010 | Carpenter |
| 2010/0312268 A1 | 12/2010 | Belson |
| 2010/0324589 A1 | 12/2010 | Carpenter et al. |
| 2011/0022076 A1 | 1/2011 | Lashinski |
| 2011/0066221 A1 | 3/2011 | White et al. |
| 2011/0282379 A1 | 11/2011 | Lee et al. |
| 2012/0046739 A1 | 2/2012 | von Oepen et al. |
| 2012/0203265 A1 | 8/2012 | Heuser |
| 2012/0289996 A1 | 11/2012 | Lee et al. |
| 2013/0231694 A1 | 9/2013 | Lashinski |
| 2014/0052170 A1 | 2/2014 | Heuser et al. |
| 2014/0094843 A1 | 4/2014 | Heuser |

FOREIGN PATENT DOCUMENTS

| | | |
|---|---|---|
| EP | 1253871 | 2/2007 |
| EP | 2303384 | 4/2011 |
| EP | 2658476 | 11/2013 |
| JP | 2011-525405 A | 9/2011 |
| WO | WO 99/23976 | 5/1999 |
| WO | WO 2004/026175 | 4/2004 |
| WO | WO 2008/100790 | 8/2008 |
| WO | WO 2008/113857 | 9/2008 |
| WO | WO 2010/008451 | 1/2010 |
| WO | WO 2010/083527 A2 | 7/2010 |
| WO | WO 2010/088520 A2 | 8/2010 |
| WO | WO 2011/034718 A2 | 3/2011 |
| WO | WO 2011/017103 A2 | 10/2011 |
| WO | WO 2012/092377 A1 | 7/2012 |

OTHER PUBLICATIONS

International Search Report in Application No. PCT/US2010/047166 dated Apr. 27, 2011, in 7 pages.

International Search Report in Application No. PCT/US20100/043390 dated Apr. 8, 2011, in 11 pages.

International Search Report in Application No. PCT/US2010/043390 dated Apr. 8, 2011, in 11 pages.

Office Action for U.S. Appl. No. 12/844,420 dated Jul. 31, 2013, in 13 pages.

Notice of Allowance for U.S. Appl. No. 12/844,420 dated Feb. 4, 2014, in 14 pages.

* cited by examiner

DUAL ENDOVASCULAR FILTER AND METHODS OF USE

CROSS-REFERENCE TO RELATED APPLICATIONS

This application is a national stage application under 35 U.S.C. §371 of PCT Application No. PCT/US2010/043390, filed on Jul. 27, 2010, which published in English as WO 2011/017103 A2 on Feb. 10, 2011 and which claims priority benefit of U.S. Provisional Application No. 61/228,703, filed Jul. 27, 2009, entitled "Dual Endovascular Filter and Methods of Use," the entire contents of which applications and publication are herein incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Endovascular procedures are being used more and more frequently to treat various cardiac and vascular surgical problems. Blocked arteries can be treated with angioplasty, endarterectomy, and/or stenting, using minimally invasive endovascular approaches. Aneurysms can be repaired by endovascular techniques. Another use for endovascular surgery is the treatment of cardiac valvular disease. A common problem in endovascular catheterization is that plaque found in the diseased vessels and valves can be dislodged and result in embolization. A major drawback to endovascular treatment of cardiac valves and arteries in the heart or thoracic aorta is that the dislodged debris can embolize into the carotid vessels resulting in catastrophic consequences such as stroke or even death. Attempts have been made to protect the cerebral vasculature with filters and other devices, but the inadequacy of the present art is obvious in the fact that these devices are rarely used. The pending patent applications for such protection devices suggests both the inadequacy of the present art and the need for improved devices not to deflect the emboli but to capture and remove the emboli from the body.

The majority of devices described are filters. The problems with filters include difficulty in placement and retrieval as well as the possibility that a filter will fill abruptly causing blockage of the artery prior to removal of the filter. Cerebral protection requires placement of filters in the carotid arteries, which has the additional drawback of manipulation of the carotid vessels during filter placement while the cerebral vasculature is still unprotected. The risk of stroke for a carotid arteriogram done by cannulation of the carotid artery is 1% compared to an arteriogram done from injection into the aorta without selective cannulation which carries minimal risk. The risk of cannulating a carotid artery, navigating a catheter containing a filter into position, and deploying the filter would likely carry an even higher stroke risk. Patients requiring cardiac or aortic arch procedures are high risk candidates for having carotid disease. The chance of causing a stroke by the placement of the protective device into both carotid arteries makes the risk of using these devices prohibitive. The time and skill necessary to selectively cannulate both carotid arteries for filter placement has also contributed to the decision not to use them despite the stroke risk of unprotected cardiac and aortic arch procedures.

BRIEF DESCRIPTION OF THE INVENTION

The present invention comprises an embolic filter device. In use, the invention is placed into the aortic arch by the access via right-radial or brachial enrty, preferably through the right arm but it may also be placed via the femoral artery or other access point used by interventional procedures such as the carotid artery. In one embodiment, the device is deployed partially in the aortic arch but also in the innominate artery and carotid artery. Additionally or alternatively, the device may deploy to protect the left subclavian artery, where the device is opened and pulled back into position to cover the ostia of both the brachiocephalic and left common carotid arteries. A portion of the device, typically extending from a common hinged frame protrudes into the vessel(s) with a portion of the device entering into the vessel or artery to trap emboli. In some embodiments the portion of the device arising from the common frame has a cone, funnel or other shape adapted or configured for positioning within the vessel lumen to filter emboli.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
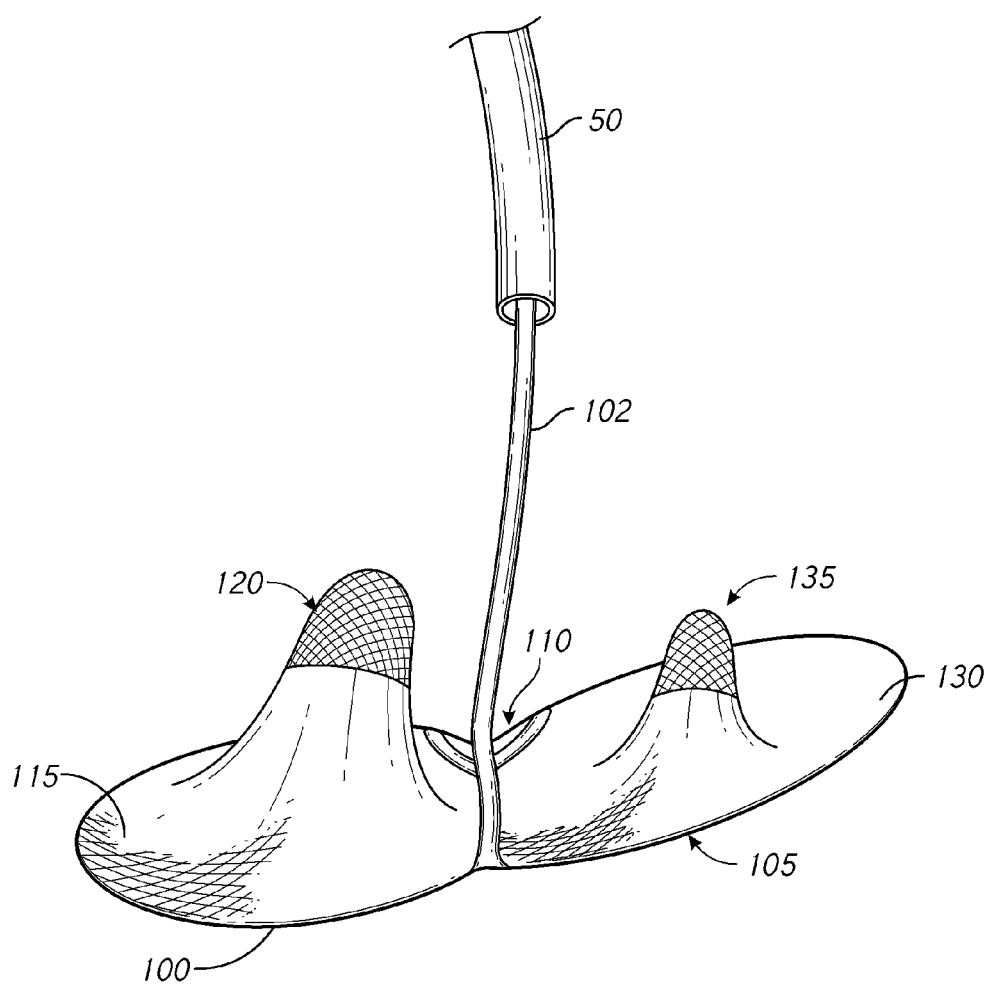
FIG. 1 depicts a schematic version of the filter device extending from the delivery catheter.

In one embodiment, filter device 100 of the present invention is positioned prior to any manipulation of the heart or thoracic aorta. FIG. 1 illustrates the filter device 100. The filter device 100 includes a frame 105 having a hinge or collapsible joint 110. The frame 105 has a generally circular shape that contains two filter portions 115, 130. The filter portions 115, 130 extend out of plane with the frame 105 into shaped sections 120, 135. The size, shape and filter characteristics of the filters 115, 130 and shaped sections 120, 135 may vary based on a number of factors such as the size, shape and relative position of the one or more vessels to be protected by the device 100 as well as the particle size selected for filtration and the desired amount of blood flow through the filter 100. These and other details of the component parts, various embodiments and uses for embodiments of the filter 100 are described below.

Figure 2:
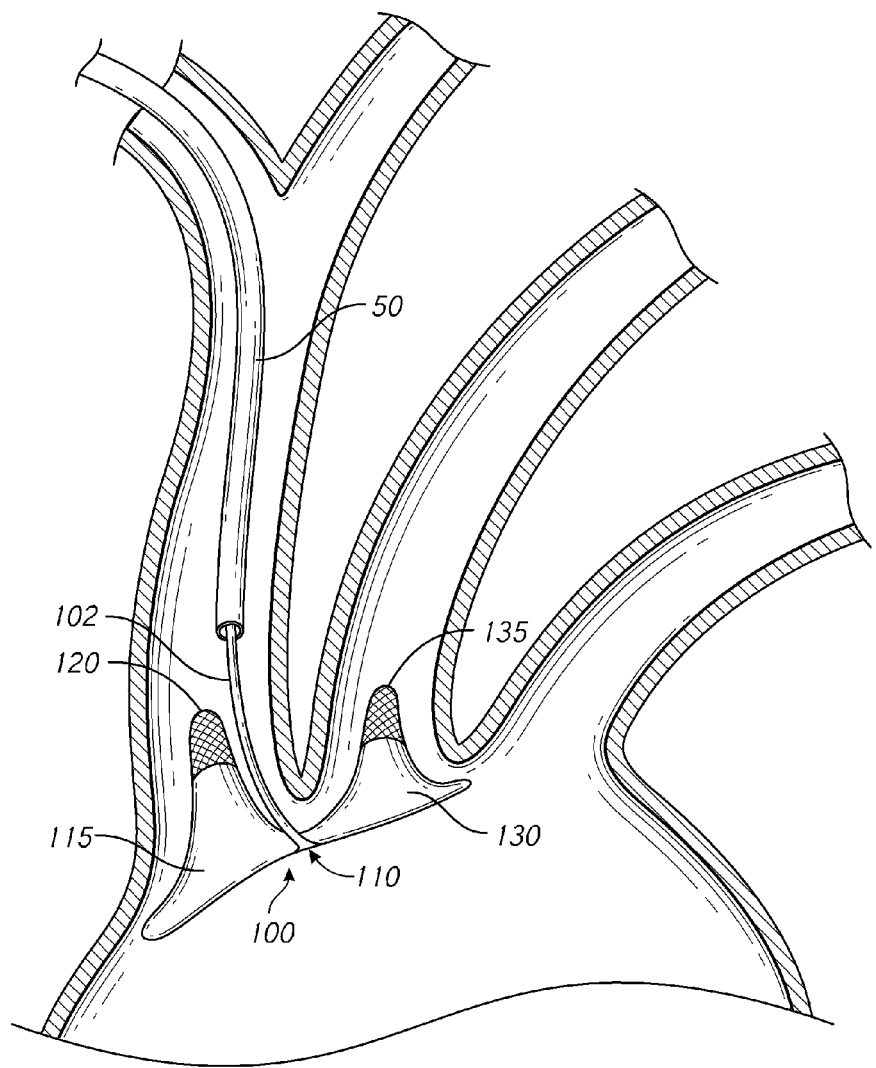
FIG. 2 depicts the filter device delivered and protecting the innominante artery and the left common carotid artery with the self expanding frame and the dome filter material protruding into each vessel.

The device 100 is simple to place and carries only the risk of catheterizing the aorta through the arm or leg, which is minimal. In use as shown in FIG. 2, the device is opened in the thoracic aorta and positioned to cover the ostia of both the inominant and left common carotid arteries and at least a portion of the device will partially enter the inominant and left common arteries. In the illustrated embodiment all or a portion of the shaped sections 120, 135 are within the protected vessel or vessels. This position prevents clots or debris from entering the cerebral circulation through either the right or left carotid arteries with one simple device. Any debris from the cardiac or aortic procedure is captured in the paraboloid of revolution shape 120, 135 protruding into each vessel from the filter 100.

Figure 3:
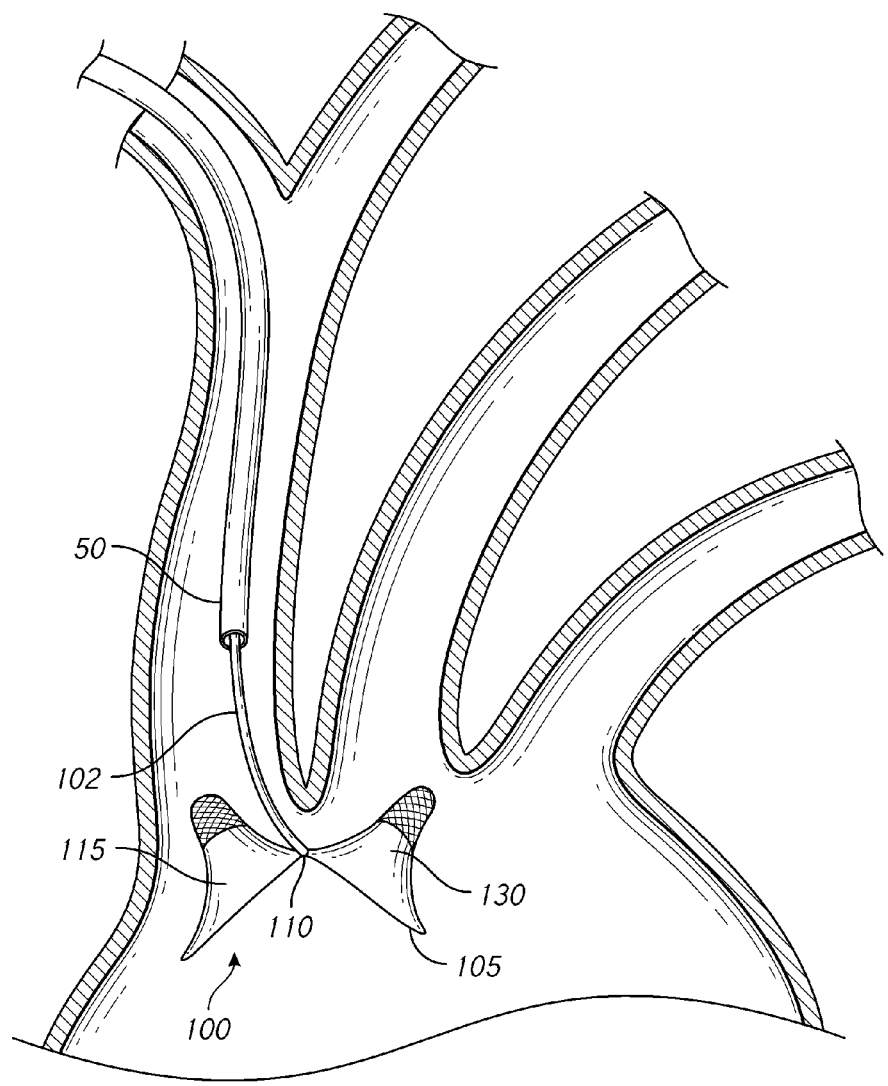
FIG. 3 depicts the device being closed and capturing the embolic material within each dome filter.
Figure 4:
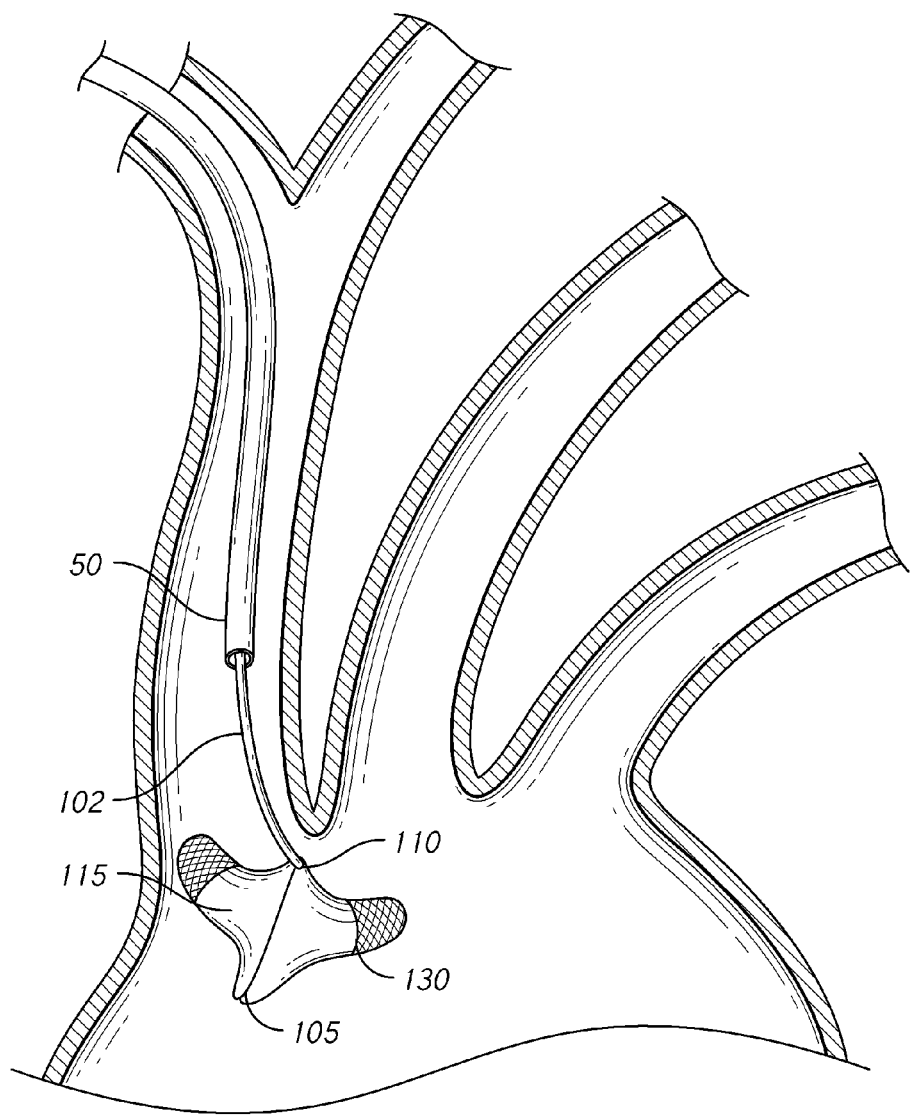
FIG. 4 depicts the domes closed at a common hinge point to trap the embolic material within the filter and ready to be withdrawn from the body.
Figure 5:
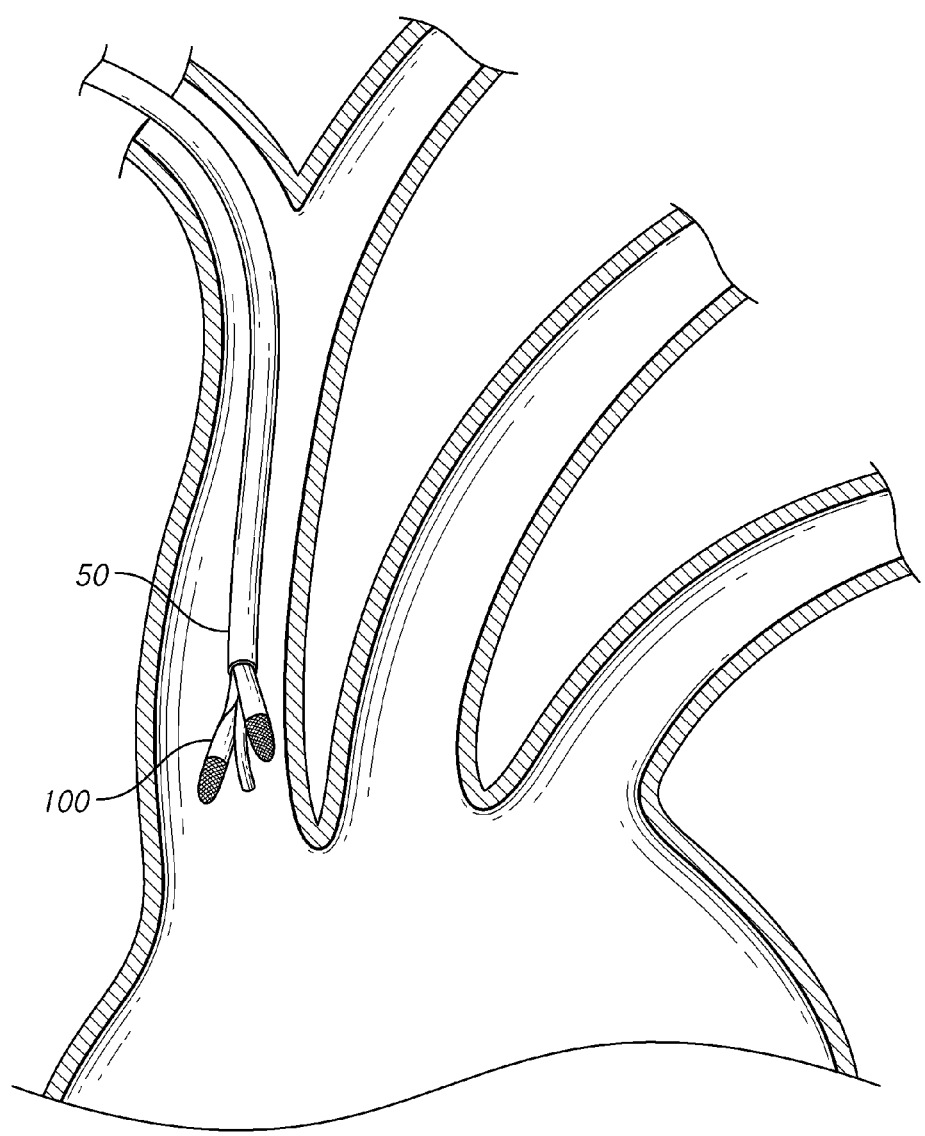
FIG. 5 depicts the filter device being drawn back into the catheter ready to be removed from the body.

After the procedure is complete, the device is inverted by means of a sheath extended over the catheter wire, which then wholly or partially covers the inverted device prior to withdrawal. As shown in FIGS. 3, 4 and 5, should any clot or debris be captured in the paraboloid of revolution 120, 135, the clot or debris will be captured when inverted via common hinge point 110 and withdrawn along with the device 100. The protrusion or depth of vessel entry of the shaped sections 120, 135 into each of the vessels may vary depending upon a number of factors such as expected particle or emboli size, amount or interaction with the filter 100. In one specific example, the shaped section portion of the filter extends from about 0.5 centimeters to about 3.0 centimeters measured from the device frame 105 positioned in the aorta. The material 115, 130 protruding into the vessel could be any suitable vascular filter material. For example, filters 115, 130 may be formed from, with or contain a polymeric material such as polyurethane with drilled holes for blood flow to the cerebral vasculature. In one aspect, the drilled holes could measure about 100 to 200 microns in diameter but preferably about 130 microns in diameter. Alternatively, the filters 115, 130 may be formed from porous material suited to trapping emboli. The material for filters 115, 130 is selected to allow for adequate filtration where the porous or drilled or formed openings will allow for sufficient blood supply to the cerebral vascular system while stopping any embolic material from traveling throughout the body circulatory system. Trapping and removal of embolic particles within filters 115, 130 rather than merely deflecting material into the aorta is believed to provide a better clinical outcome for the patients. Embolic particles simply deflected back into the aorta will eventually block other blood vessels elsewhere in the body such as the kidneys or lower extremities. As such, embodiments of the device 100 may advantageously be employed to filter out, capture and then remove emboli while also keeping the aorta relatively clear. As best seen in FIG. 2, the frame 110 only remains in the aorta since the filters 115, 130 extend substantially above the plane of frame 105.

The device is preferably concaved-shape with an adequate area to cover the ostia of both the brachiocephalic and left common carotid arteries (FIGS. 1 and 2). The filters 115, 130 may be made of a material with pores (100 to 200 micron) or similar openings or permeability to allow the flow of blood into the cerebral circulation, but able to deflect or trap particles of a size which could cause a stroke. The edge of the frame 105 is preferably a flexible, porous donut shape allowing a good seal with the curved aortic wall. In some embodiments, the edge of the frame 105 will preferably contain a nitinol wire ring or other self-expanding material. The device may have struts or ribs positioned on, in or within frame 105 to assist in the opening and closing of the device and to help maintain its position in use. The device may also be made to open as a result of its construction material, for example, nitinol or polymer, elastically resuming its shape after being released from its sheath.

When the device is to be closed, a tube or sheath is extended over the guide wire until it engages the device. Next, the device is pulled back so that it inverts and is enclosed in the tube for removal (FIGS. 3 and 4). Inverting the device so that the filter openings for each of the filters 115, 130 assures that no trapped particles within filters 115, 130 such as within shaped sections 120, 135 escape into the bloodstream. The components of the device 100 may optionally be constructed of polymer, fabric, metal, or a combination of these or other suitable biocompatible materials. The device may also optionally be equipped with radio-opaque markers or other structural parts which are radio-opaque for aid in placement guidance and/or positioning within the body.

Another embodiment of the device has a rolled edge.

The device may also have a flat porous edge.

Another embodiment of the device has no struts, but instead has a nitinol skeleton.

Another embodiment has multiple wires to position and anchor the device.

Another embodiment of the device has anchors at the edges which help to maintain its position during the procedure.

Another embodiment of the device is parachute-like, with a ring gasket at its edge. The gasket can be a softer material such as, for example without limitation, a silicone polymer or an inflatable membrane such as a balloon member. The profile of an inflatable gasket is generally relatively small and when inflated increases in profile, sealing the contacted portion surrounding the protected vessels. The inflation can be pressurized from the handle portion at the proximal end of the device external to the body with, for example a common endoflator used in interventional cardiology. The gasket would be held firmly in position over the ostia of the brachiocephalic and left common carotid arteries. The billowy porous middle section would deflect or trap clot and debris on its exterior surface while causing minimal resistance in the aorta. The middle portion would be inverted as it is removed by pulling on wires attached to its center, capturing any clot stuck to it.

Alternatively, the center of the device may comprise a screen, which fits more snugly against the aortic wall, with a very small profile, further preventing resistance to downstream aortic bloodflow. Again the device would be removed by inversion, capturing any debris stuck to it prior to removal.

The device may be round, oval or rectangular or of another shape to assist in sealing of the edge against the wall of the aorta, covering the ostia of both the brachiocephalic and left common carotid arteries and maintaining a low profile within the lumen of the aorta.

This device could be modified in size in another embodiment in order to be used to cover the ostia of different vessels.

The device may be coated with materials or pharmalogically active agents that prevent or impair clot formation (e.g., heparin or any other suitable anticoagulant).

The device may be deployed through an artery of the arm, or through the femoral artery. The preferred method would be through the right arm, if possible, as this would allow the device to be pulled back against the aortic wall to place it.

When deployed through the femoral artery, the opening of the device would be different and the device would be pushed against the aortic wall over the brachiocephalic and left common carotid openings rather than being pulled back. A wire would be cannulated into the brachiocephalic artery in this case to ensure correct positioning of the device. The device would be modified to allow this method of delivery and positioning. In one aspect, retrieval of the device would involve inversion and closing of the device by drawstring or another method. For example, pulling, activating, manipulating or otherwise causing movement of the common hinge or frame joint 110.

Brachial Artery Insertion of the Device

The device is delivered via percutaneous insertion into the right brachial artery and is guided into the aortic arch. There it is deployed and then pulled back into position to cover the ostia of the innominate and left common carotid arteries. The device deflects and filters embolic debris during aortic and cardiac procedures, allowing the flow of blood through into the cerebral circulation (carotid arteries) but not permitting the passage of particulate debris.

Femoral Artery Insertion of the Device

The device is delivered via percutaneous insertion into the femoral artery and is guided into the aortic arch. After catheterization of the innominate artery, the device is passed over the wire and brought into position covering the ostia of the innominate and left common carotid arteries.

Deployment of the Device via Arm Approach

Percutaneous access to the circulation via the right arm is performed and a wire guided into the aortic arch after exiting the innominate artery. The device may be placed over the wire or advanced without a guidewire and guided into the aortic arch. The covering outer sheath which encapsulates the device is retracted, exposing the device to the aortic bloodstream. The device is then opened in the aortic arch. The device is pulled back into position, covering the ostia of the innominate and left common carotid artery with a portion of the device entering into each vessel. The device allows the passage of blood through to the carotid arteries, but deflects debris passing along the aorta and filtering any embolic material entering the innominante and left common carotid arteries. At the completion of the debris producing concomitant procedure, the device is closed by inverting the two domes 120, 135. The device is then withdrawn into a covering sheath (FIG. 5) to completely encapsulate it prior to removal from the arm access artery. Any trapped debris is captured in the domes, safely and securely within the catheter.

Embolic Filtration Device

Figure 8:
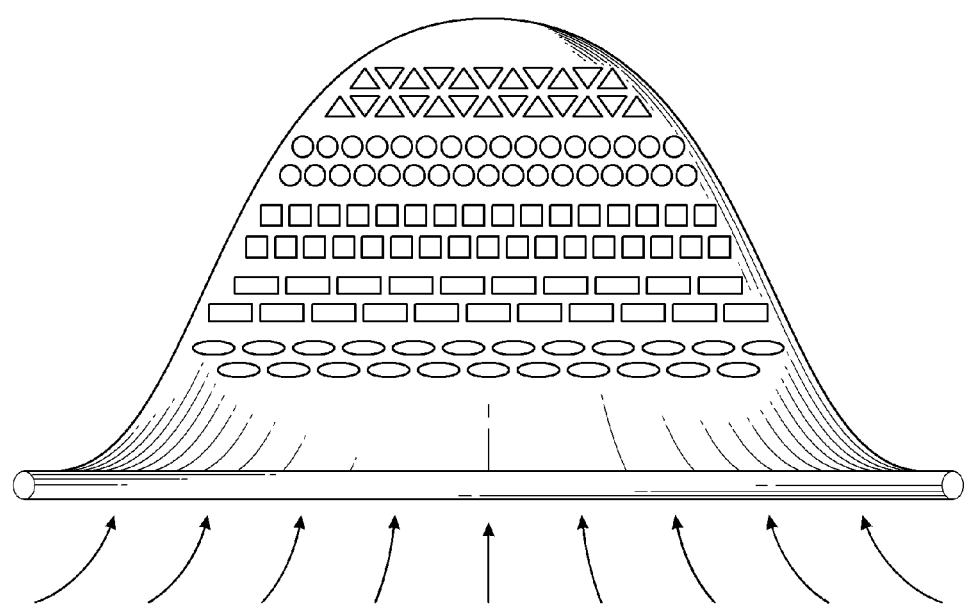
FIG. 8 illustrates a variety of exemplary shapes, sizes, and configurations of holes that can be formed in one or more of the filters.

The device of the present invention, viewed from above, is semi-circular or oval in shape with an adequate diameter of about 15 mm to about 30 mm in the short axis and about 20 mm to about 60 mm in the long axis to cover the ostia of both the brachiocephalic and left common carotid arteries. The filter material may be a polymeric material such as polyurethane or other thin material with a porosity that will allow the flow of blood, but capture particles of a size which could cause a stroke. FIG. 8 illustrates exemplary sizes, shapes, and configuration of the holes that can be formed in a filter. The size and configuration of the holes in the filter could be round in shape but more effectively would be an oval or a slot configuration where the material captured would be smaller but the surface area of the openings could be larger. Other shapes could include triangular or squares to achieve the same function. A square hole would provide about 30 percent more cross sectional area for blood to flow while still capturing the same spherical particle size. The edge of the device is a flexible, porous donut, similar to the edge of a diaphragm, allowing a good seal with the curved aortic wall. The edge will preferably contain a self-expanding material such as Nitinol. The frame of the device may also include struts to assist in the opening and closing of the device and/or to help maintain its position in the relevant anatomy.

The device is constructed of polymer, fabric, metal, or a combination of these materials. The device may be provided with radioopaque markers or metal parts which are radioopaque.

Another embodiment of the device has a rolled edge. The device could also have a flat porous edge. Another embodiment of the device has no struts, but a nitinol skeleton. Another embodiment has multiple wires to position and anchor the device. Another embodiment of the device has anchors at the edges which help to maintain its position during the procedure.

Another embodiment of the device is parachute-like, with a ring gasket at its edge. The gasket would be held firmly in position over the ostia of the brachiocephalic and left common carotid arteries.

Embodiments of the filter 100 may be configured for self locking and/or self sealing with or within the anatomy of the filter site. Self lock or self sealing may be accomplished by releasing a stowed filter from a sheath or other restraint or otherwise activity or actuating the device into a locked or sealing configuration.

Alternatively, the filter may be released into the vasculature and then urged into a locked or sealed configuration. In one aspect, a locking device is positioned outside the body that is adapted and configured to permit movement of or adjusted to the filter relative to the filter site to seal and/or lock the position and configuration of the filter. When the desired position and configuration is achieved the external locking device is used to hold the filter in position and maintain the desired configuration.

Figure 6:
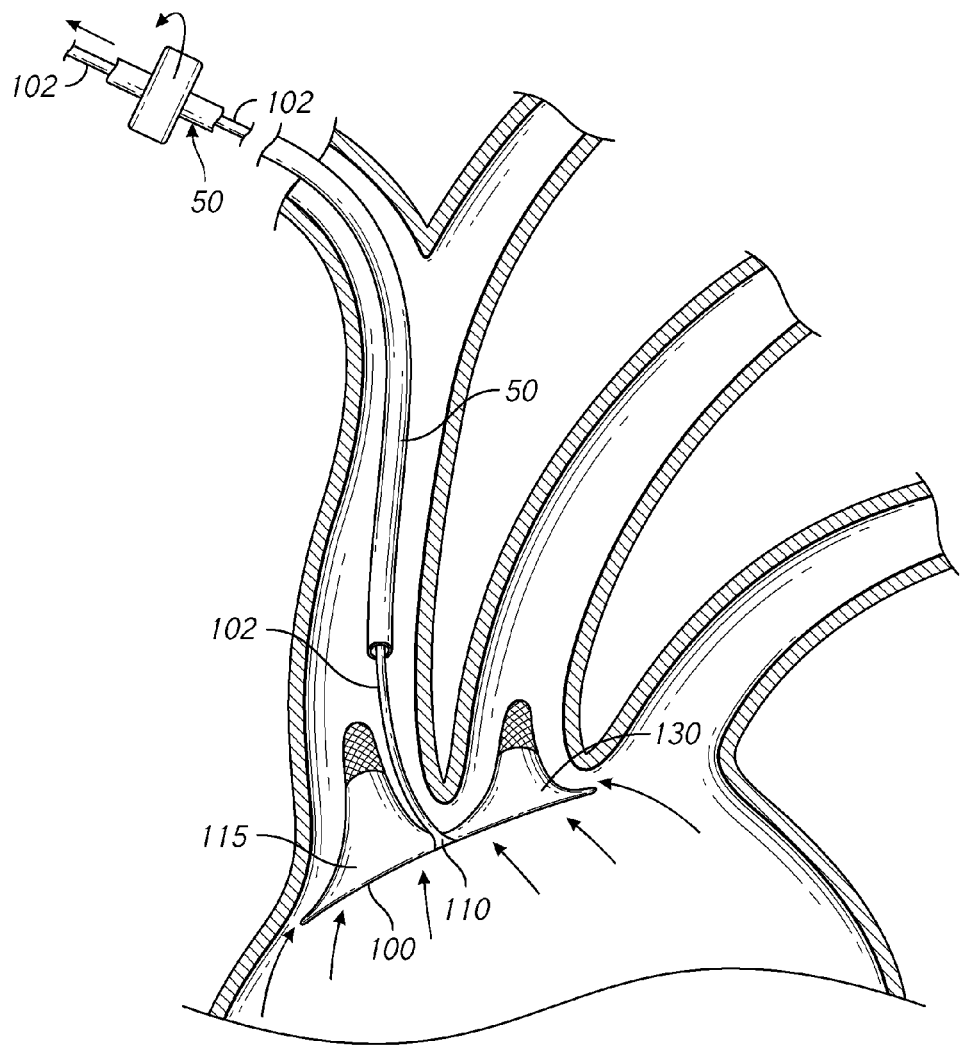
FIG. 6 illustrates a filter positioned within the aorta and connected to a locking device (unlocked configuration).
Figure 7:
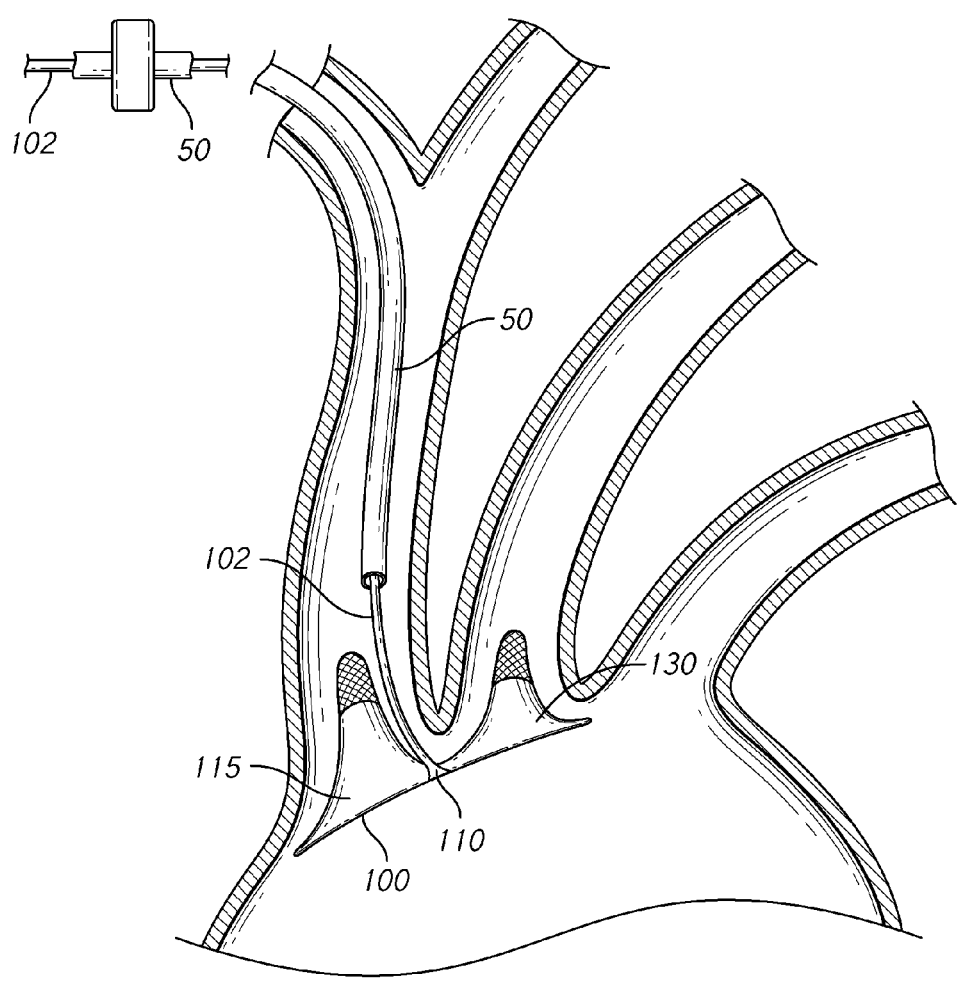
FIG. 7 illustrates the filter of FIG. 6 after tensioning the filter into a sealing arrangement within the aorta and protected vessels and restraining the filter with the locking device (locked configuration).

In one specific aspect, once the desired filter device position is obtained, a locking mechanism relative to the body could hold tension between the device and the aortic wall to maintain a proper blood seal. This could be achieved by tensioning the connection of the device within the body via delivery catheter and a clamp or fixation device between the introducer sheath and tensioned member. A good example of this would be a RHV (rotating hemostaic valve) mounted to the introducer sheath allowing the tensioned connection member to pass through the central lumen. As the tension is added to the central member the RHV could be rotated causing an interference force between the two creating a lock where the tension is now carried by the introducer sheath which is external to the body and the internal filter device which is held in tension along the aortic wall without constant human interaction pulling the device relative to the introducer sheath now needed. Turning now to the example of FIGS. 6 and 7. FIG. 6 illustrates the filter deployed within the aorta but not yet sealed with the anatomy. A locking mechanism, here a rotating hemostasis valve, is used to allow movement between and lock the relative position of the element connected to the filter (i.e. a guidewire) and the sheath used to deliver the filter. After pulling the filter into a sealing arrangement with the appropriate vessels, the RHV may be locked thereby securing the filter relative to the sheath and the entire device relative to the anatomy. The RHV in the illustrative embodiment may be replaced by any suitable locking device that provides the adjustment, sealing and securing characteristics described above.

The billowy porous middle section would deflect or trap clot and debris on its exterior surface while causing minimal resistance in the aorta. The middle portion would be inverted as it is removed by pulling on wires attached to its center, capturing any clot stuck to it. Alternatively, the center of the device could be a screen, which fits more snugly against the aortic wall, with a very small profile, further preventing resistance. Again the device would be removed by inversion, capturing any clot stuck to it prior to removal.

The device may be round, oval or rectangular or of another shape to assist in sealing of the edge against the wall of the aorta, covering the ostia of both the brachiocephalic and left common carotid arteries and maintaining a low profile within the lumen of the aorta. This device could be modified in size in another embodiment in order to be used to cover the ostia of different vessels. The device may be coated with something which prevents clots (e.g. heparin).

Any of the features of the filter devices and methods of use described herein can be incorporated into any of the filter devices and methods of use described in U.S. Patent Publication No. 2010/0179647, U.S. Patent Publication No. 2010/0179585, U.S. Patent Publication No. 2010/0179584, U.S. Patent Publication No. 2010/00179583, and U.S. Patent Publication No. 2008/0065145 (and vice versa), all of which are incorporated by reference herein. For example, the disclosure herein includes embodiments in which the emboli deflection element from the Patent Applications recited above is replaced with first and second emboli trapping filters, examples of which are described herein.

While the invention has been described in its preferred embodiments, it is to be understood that the words which have been used are words of description rather than of limitation and that changes may be made within the purview of the appended claims without departing from the true scope and spirit of the invention in its broader aspects. Rather, various modifications may be made in the details within the scope and range of equivalents of the claims and without departing from the spirit of the invention. The inventor further requires that the scope accorded the claims be in accordance with the broadest possible construction available under the law as it exists on the date of filing hereof (and of the application from which this application obtains priority, if any) and that no narrowing of the scope of the appended claims be allowed due to subsequent changes in the law, as such a narrowing would constitute an ex post facto adjudication, and a taking without due process or just compensation.

What is claimed is:

1. An embolic filter device, comprising:
   a deployment sheath having a longitudinal axis;
   a frame having a delivery configuration and a deployed configuration, the frame comprising a first frame portion and a second frame portion;
   a first filter portion coupled to the first frame portion and a second filter portion coupled to the second frame portion wherein the first and second filter portions each have an open portion and a closed portion, wherein the open portion is adapted to allow foreign particles to pass therethrough and the closed portion is adapted to trap foreign particles therein;
   wherein the first and second frame portions pivot about a joint positioned between the first and second frame portions closest to each other, an axis of the joint extending substantially perpendicular to the longitudinal axis of the deployment sheath, thereby pivoting the open portions of the first and second filter portions towards one another about the axis and reconfiguring the frame into the delivery configuration in which the open portions of the first and second filter portions face each other and wherein in the deployed configuration the first and second frame portions are substantially perpendicular to the position of the first and second frames in the delivery configuration and wherein the open portions face away from the deployment sheath in the deployed configuration.

2. The filter device of claim 1, further comprising an elongate delivery member secured to the frame.

3. The filter device of claim 1, wherein the closed portions of the first and second filter portions extend about 0.5 cm to about 3 cm from the frame.

4. The filter device of claim 1, wherein the first and second filter portions are generally dome shaped.

5. The device of claim 1, further comprising a delivery device through which the frame and the first and second filter portions are adapted to be delivered, and further comprising a lock to lock the frame relative to the delivery device.

6. The device of claim 1, where the frame and the first and second filter portions have an aspect ratio of at least about 2:1.

7. The device of claim 1, wherein the first and second filter portions are both concave.

8. A method of protecting a cerebral vasculature of a patient, comprising:
   advancing a delivery device with a filter device positioned therein through a first vessel, the filter device comprising a frame and first and second filter portions secured to the frame, wherein the frame has a folded configuration and a deployed configuration;
   deploying the filter device from the delivery device;
   positioning the first filter portion relative to the first vessel such that foreign particles traveling into the first vessel will be trapped in the first filter portion; and
   with the delivery device positioned in the first vessel, positioning the second filter portion relative to a second vessel such that foreign particles traveling into the second vessel will be trapped in the second filter portion.

9. The method of claim 8, wherein the first and second filter portions each have an open portion and a closed portion, and wherein the positioning steps comprise positioning the first closed portion in the first vessel and positioning the second closed portion in the second vessel.

10. The method of claim 9, wherein positioning steps comprise positioning the closed portions-about 0.5 cm to about 3 cm from the frame.

11. The method of claim 8, wherein the deploying step comprises deploying the filter device from within the delivery device to allow the frame to reconfigure from the folded configuration to the deployed configuration.

12. The method of claim 8, further comprising creating a seal between the first and second vessels and the filter device by proximally retracting the frame into contact with tissue.

13. The method of claim 8, further comprising locking the position of the filter device relative to tissue.

14. The method of claim 8, wherein the deployed step comprises allowing the frame to reconfigure from the folded configuration to the deployed configuration.

15. The method of claim 8, further comprising folding the frame from the deployed configuration to the folded configuration, wherein folding the frame prevents foreign particles from being released from the first and second filter portions.

* * * * *

UNITED STATES PATENT AND TRADEMARK OFFICE
CERTIFICATE OF CORRECTION

| | | |
|---|---|---|
| PATENT NO. | : 8,974,489 B2 | Page 1 of 1 |
| APPLICATION NO. | : 13/383488 | |
| DATED | : March 10, 2015 | |
| INVENTOR(S) | : Randall T. Lashinski | |

It is certified that error appears in the above-identified patent and that said Letters Patent is hereby corrected as shown below:

In the specification

In column 2 at line 9, Change "enrty," to --entry,--.

In column 2 at line 38, Change "innominante" to --innominate--.

In column 3 at line 13, Change "inominant" to --innominate--.

In column 3 at line 14, Change "inominant" to --innominate--.

In column 5 at line 41, Change "innominante" to --innominate--.

In column 5 at line 48, Change "Filteration" to --Filtration--.

In column 6 at line 8, Change "radioopaque" to --radio-opaque--.

In column 6 at line 9, Change "radioopaque" to --radio-opaque--.

In column 6 at line 43, Change "hemostaic" to --hemostatic--.

In the claims

In column 8 at line 45, In Claim 10, change "portions-about" to --portions about--.

Signed and Sealed this
Twenty-fourth Day of November, 2015

Michelle K. Lee
*Director of the United States Patent and Trademark Office*